(12) United States Patent
Steg

(10) Patent No.: US 6,322,546 B1
(45) Date of Patent: Nov. 27, 2001

(54) FLUID CONTROL CONDUIT

(75) Inventor: Robert Steg, Escondido, CA (US)

(73) Assignee: Jostra Bentley Inc., PR (US)

( * ) Notice: Subject to any disclaimer, the term of this patent is extended or adjusted under 35 U.S.C. 154(b) by 0 days.

(21) Appl. No.: 09/429,773

(22) Filed: Oct. 28, 1999

(51) Int. Cl.[7] .................................................. A61M 1/00
(52) U.S. Cl. ................................................ 604/319; 604/4
(58) Field of Search .............................. 604/4, 319, 321, 604/326, 327, 403, 407, 905; 251/12, 14, 24, 63.4, 142; 137/808, 810, 811, 813; 600/573

(56) References Cited

U.S. PATENT DOCUMENTS

| | | | |
|---|---|---|---|
| 4,533,516 | 8/1985 | Johnsson et al. ...................... 422/46 |
| 4,737,139 | 4/1988 | Zupkas et al. . | |
| 5,024,613 | * 6/1991 | Vasconcellos et al. ................... 604/4 |
| 5,034,188 | 7/1991 | Nakanishi et al. ..................... 422/46 |
| 5,087,250 | * 2/1992 | Lichte et al. .......................... 604/321 |
| 5,149,318 | * 9/1992 | Lindsay .................................. 604/4 |
| 5,158,533 | * 10/1992 | Strauss et al. ............................ 604/4 |
| 5,192,439 | * 3/1993 | Roth et al. ............................. 210/485 |
| 5,254,080 | * 10/1993 | Lindsay .................................... 604/4 |
| 5,282,783 | 2/1994 | Lindsay .................................... 604/4 |
| 5,580,349 | 12/1996 | Thor et al. . | |
| 5,725,516 | * 3/1998 | Cook et al. ........................... 604/319 |
| 5,759,396 | * 6/1998 | Van Driel ............................. 210/315 |
| 5,792,126 | * 8/1998 | Tribastone et al. .................. 604/319 |
| 5,800,721 | 9/1998 | McBride ............................... 210/506 |

* cited by examiner

Primary Examiner—John G. Weiss
Assistant Examiner—David J. Cho
(74) Attorney, Agent, or Firm—Christie, Parker & Hale LLP

(57) ABSTRACT

A design and method of operation are disclosed for a fluid control conduit of a blood reservoir. The venous blood inflow conduit includes a fluid control nozzle and a base. When assembled together the nozzle and base form a trap feature which prevents reflux of air or other gas upwardly into the nozzle of the conduit. As a result, during use of the reservoir the conduit normally runs full of venous blood and turbulence of the blood is prevented. In addition, the conduit also functions to divert the downward flowing venous blood in the nozzle into the base at an optimum fluid velocity to overcome the buoyancy effect of air or gas bubbles within the blood.

26 Claims, 6 Drawing Sheets

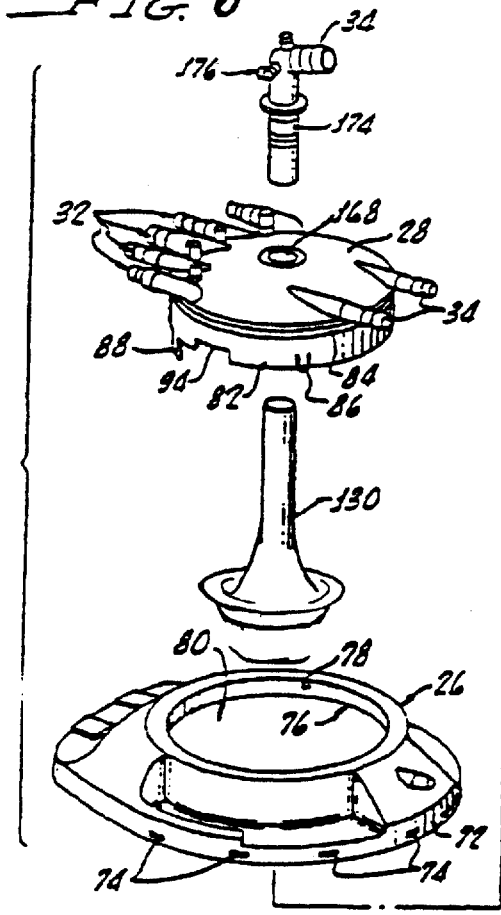
Fig. 6
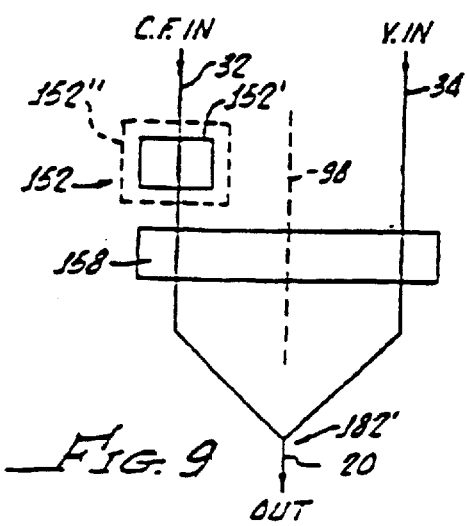
Fig. 9
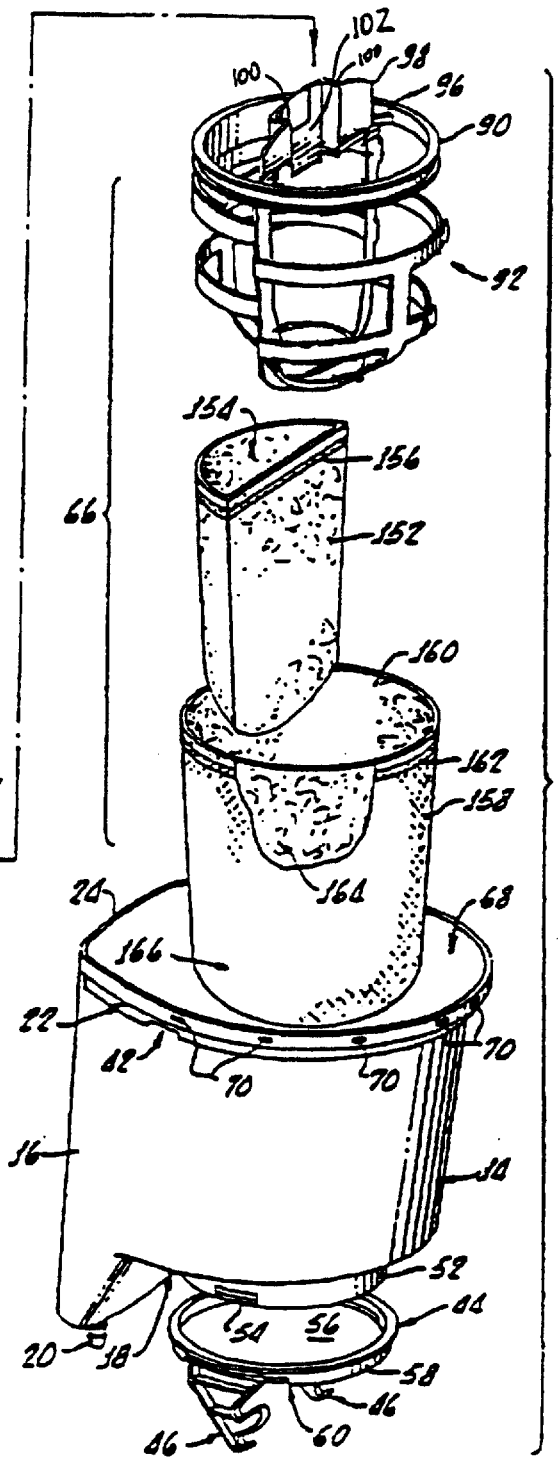

FLUID CONTROL CONDUIT

FIELD OF THE INVENTION

The present invention relates to reservoir systems used during surgery and methods for using such systems during surgical procedures. The present invention particularly relates to a fluid control conduit of a blood reservoir used to receive blood from the circulatory system of the patient (venous blood) and methods of operation of such fluid control conduit.

BACKGROUND OF THE INVENTION

The recovery of cardiotomy fluid and venous blood during a cardiopulmonary bypass procedure involves collecting the fluid and blood in a reservoir and treating such fluid and blood for reinfusion into the patient. Treatment of the cardiotomy fluid and venous blood may include oxygenation, temperature control and circulatory pumping in a life sustaining extracorporeal blood flow. The cardiotomy fluid recovered from a surgical site additionally requires treatment to remove foreign material that is collected at the wound site by exposure to air and generated during the surgical procedure (i.e., tissue particles, blood clots or bone fragments, as well particulates from foreign body exposure, for example). Similarly, the venous blood received from the circulatory system is also treated to ensure that any entrained bubbles of gas created by extracorporeal circulation are removed. After treatment, the collected blood and cardiotomy fluid are returned to the patient via the extracorporeal circuit.

A variety of conventional separate or combined cardiotomy fluid and venous blood reservoirs have been developed to collect and treat cardiotomy fluid and venous blood during a surgical procedure. Typically, cardiotomy fluid collected within the reservoir is first subjected to a defoaming step by a defoamer element and then to a filtering step by a depth filter element. The cardiotomy fluid must be filtered and defoamed to remove air, debris and clots generated during the procedure. Since additional air bubbles may be created as the fluid flows through the filter element, the cardiotomy fluid often undergoes a subsequent defoaming step in a second defoamer element prior to reinfusion into the patient.

Venous blood collected in the reservoir must also be filtered and defoamed prior to being reinfused. However, there are two main differences between venous blood and cardiotomy fluid. First, unlike cardiotomy fluid, venous blood is relatively free of foreign material and clots. As a result, venous blood collected within the reservoir requires only minimal defoaming and filtration. Second, the flow rate of venous blood is, in general, significantly greater than the flow rate of cardiotomy fluid. Forcing venous blood together with cardiotomy fluid through the depth filter element used for cardiotomy fluid could damage healthy venous blood cells. Therefore, it is preferred to have specific filter and defoamer elements for cardiotomy fluid and separate filter and defoamer elements for venous blood. Alternatively, the same filter and defoamer elements can be used for both cardiotomy fluid and venous blood provided that the cardiotomy fluid and venous blood maintain separate flow paths through the filter and defoamer elements in the reservoir.

The formation of air and gas bubbles in conventional cardiotomy fluid and venous blood reservoirs is a common and on-going problem. Since the presence of air bubbles in the patient's vascular system may cause various life-threatening conditions, it is vital that all air or gas bubbles entrained in the venous blood and cardiotomy fluid are removed prior to reinfusing the fluid and blood into the patient. Conventional cardiotomy fluid and venous blood reservoirs incorporate various filters, defoamers, screens and similar devices in a variety of shapes and configurations to facilitate trapping and removal of bubbles from the fluid and blood.

An example of such a cardiotomy fluid and venous blood reservoir can be found in U.S. Pat. No. 4,737,139, issued Apr. 12, 1988, to Paul F. Zupkas et al. (the '139 patent). The '139 patent discloses a reservoir that includes upper and lower chambers which are vertically separated by a horizontal ring-like portion of a support member. The cardiotomy fluid which is received by an upper inlet is subjected first to a defoaming step by a defoamer and then to a filtering step by a depth filter element. Finally, the fluid is again defoamed by a defoamer element which is surrounded by a mesh. The venous blood is defoamed by a lower portion of the defoamer element which is shared with the cardiotomy fluid in parallel but fluidly separate flow paths. After flowing radially outwardly through the defoamer element, both cardiotomy fluid and venous blood flow into a common chamber for return to the patient via a lower outlet of the housing.

The cardiotomy fluid defoamer and filter elements and the venous blood defoamer and filter elements of the '139 patent have substantially the same diameter. Therefore, the effective defoamer areas in each of the venous blood and cardiotomy fluid flow paths are a function of the fractions of the height of the device which are devoted to each flow path. However, since the cardiotomy fluid filter element must have sufficient area to pass the necessary fluid volume both at the beginning of use when the filter is clean and unobstructed and also after a period of use as the filter becomes partially clogged, the ratio of cardiotomy filter area versus volume for the reservoir taught by the '139 patent is or can be unfavorable. In other words, because of the common diameters of the filters and defoamers in these conventional reservoir designs, the area available to the cardiotomy filter is simply a function of that part of the height of the device which is devoted to treatment of cardiotomy fluid. Thus, the device either has to be made very tall, or most of the height of the device must be allocated to the cardiotomy fluid flow path. As a result, the defoamer area for the venous blood flow path may be undesirably small thereby effecting insufficient bubble removal.

A more recent reservoir design has been proposed in U.S. Pat. No. 5,580,349 to address some of the aforesaid drawbacks. The reservoir design in this patent utilizes a screen, such as a polyester mesh sheet, disposed between two flexible sheets so as to form an input chamber, output chamber and common vent chamber. During use, blood pumped into the input chamber moves upward through the chamber, reaches an apex, and then falls toward the bottom of the reservoir. As the blood moves upward, gas bubbles, including micro-emboli, entrained in the blood are also directed upward. The buoyancy of the bubbles causes the bubbles to escape through the vent chamber as the blood drops to the bottom of the reservoir. In addition, the porous screen which separates the two chambers further enhances bubble separation from the blood as the blood flows along the screen. Although this design provides a means for removing bubbles from cardiotomy fluid and venous blood in a reservoir, it has some inherent shortcomings.

For example, as the fluid and blood fall toward the bottom of the output chamber, at a fluid velocity of approximately 0.9 m/s, backsplash and eddy formation within the reservoir may occur when the fluid and blood hit the bottom of the chamber. As a result, new bubbles may be generated in the output chamber of the reservoir. In addition, the porous surface of the mesh also agitates the downward flowing blood, further contributing to the formation of turbulence and, consequently, bubbles in the fluid and blood. Therefore, there is a potential risk that air or gas bubbles entrained in the fluid and blood may be infused into the patient.

In view of the foregoing, it is apparent that a variety of cardiotomy fluid and venous blood reservoir designs have been developed in an attempt to effectively and efficiently filter and defoam cardiotomy fluid and venous blood prior to being reinfused into the patient. It is also apparent, however, that these reservoir designs still require improvement, particularly as it relates to the reduction and/or elimination of gas and air bubbles in the fluid and blood. In particular, it is apparent that there is a continuing need to provide a blood reservoir with a more effective design that reduces or eliminates turbulence and/or eddy formation and minimizes resultant bubble formation as blood flows through the reservoir. There is also a need to provide a method of treating both cardiotomy fluid and venous blood to safely and effectively remove air or gas bubbles entrained in the blood prior to reinfusing, the blood into a patient.

OBJECTS AND SUMMARY OF THE INVENTION

It is an object of the present invention to provide an improved fluid conduit (for example, a blood conduit) that can be used in a fluid reservoir, such as a venous blood reservoir or a combined cardiotomy fluid and venous blood reservoir.

It is another object of the present invention to provide a fluid conduit for use in a blood reservoir that reduces fluid velocity and keeps the wall shear stress and turbulence low.

It is further object of the present invention to provide a blood reservoir with a fluid flow path which is relatively free of discharge turbulence.

It is yet another object of the present invention to provide a fluid conduit in a blood reservoir that decreases or eliminates bubble formation in the reservoir.

According to one aspect of the present invention, an improved fluid conduit for use in a blood reservoir comprises a base and a nozzle. Preferably, the base is shaped to include an axially aligned center peak and trough and the nozzle is shaped so that its internal radial diameter increases in a downward/vertical direction along the length of the nozzle. An upper end of the nozzle connects to a blood inlet and a lower portion of the nozzle is aligned with and located onto the base of the blood conduit. In a preferred embodiment, the wall of the fluid control nozzle includes a gradual slope that extends continuously and radially outward from its axial centerline. The gradual slope along the conduit reduces fluid velocity and keeps the wall shear stress and turbulence low. As a result, the formation of shear-induced platelet aggregates in the blood is reduced.

According to another aspect of the present invention a trap is formed between the top of the lower portion of the nozzle and the locating edge of the base of the conduit. The trap feature prevents reflux of air or other gases upwardly into the nozzle of the conduit which decreases fluid turbulence and resulting bubble formation in the reservoir. During normal use of the reservoir, the conduit runs full of venous blood and, as a result, both splashing of blood as well as the possibility of an air embolism from air reflux into the circulatory system are prevented.

Accoring, to a further aspect of the present invention, a fluid control conduit includes a novel center peak that functions to direct the downward flowing venous blood in the nozzle into the base at an optimum fluid velocity to overcome the buoyancy affect of air or gas bubbles within the blood. This feature also prevents the formation or generation of smaller bubbles which are typically generated from the considerable fluid turbulence and free surface created from larger air or gas bubbles that may be trapped in said conduit.

The present invention also provides a preferred method of treating venous blood in a blood reservoir. The method comprises channeling venous blood into a reservoir through one or more inlets at an upper end of the reservoir, flowing the blood through a nozzle of a blood inflow conduit and directing the blood between a lower portion of the nozzle and base of the fluid control conduit. The method may further include defoaming the blood using a liquid permeable filtering element prior to flowing the blood out of an outlet of the reservoir and reinfusing the blood into a patient.

Further objects and advantages of the present invention shall become apparent to those skilled in the art upon reading and understanding the following detailed description of the present invention.

BRIEF DESCRIPTION OF THE DRAWINGS

Other features and advantages of the present invention will be seen as the following description of particular embodiments progresses in conjunction with the drawings, in which:

FIG. 6 is an exploded perspective view of the exemplary cardiotomy fluid and venous blood reservoir of the present invention;

FIG. 9 provides a schematic of a tributary confluent blood fluid flow circuit of a blood reservoir in accordance with a preferred embodiment of the present invention.

DETAILED DESCRIPTION OF THE INVENTION

The present invention comprises an improved fluid control conduit for use in a fluid reservoir. In an exemplary embodiment, the fluid control conduit is used in a venous blood reservoir, such as the venous blood reservoir shown in FIG. 1. In general, the fluid control conduit (not shown) of the venous blood reservoir 1 is fluidly connected to the inlet port 2, which receives venous blood from the patient, and the outlet port 3, from which filtered venous blood exits the reservoir and is consequently reinfused into the patient. The venous blood reservoir also includes a defoamer and/or filter (not shown) to deform and/or filter the collected venous blood before it is reinifised into the patient.

Figure 1:
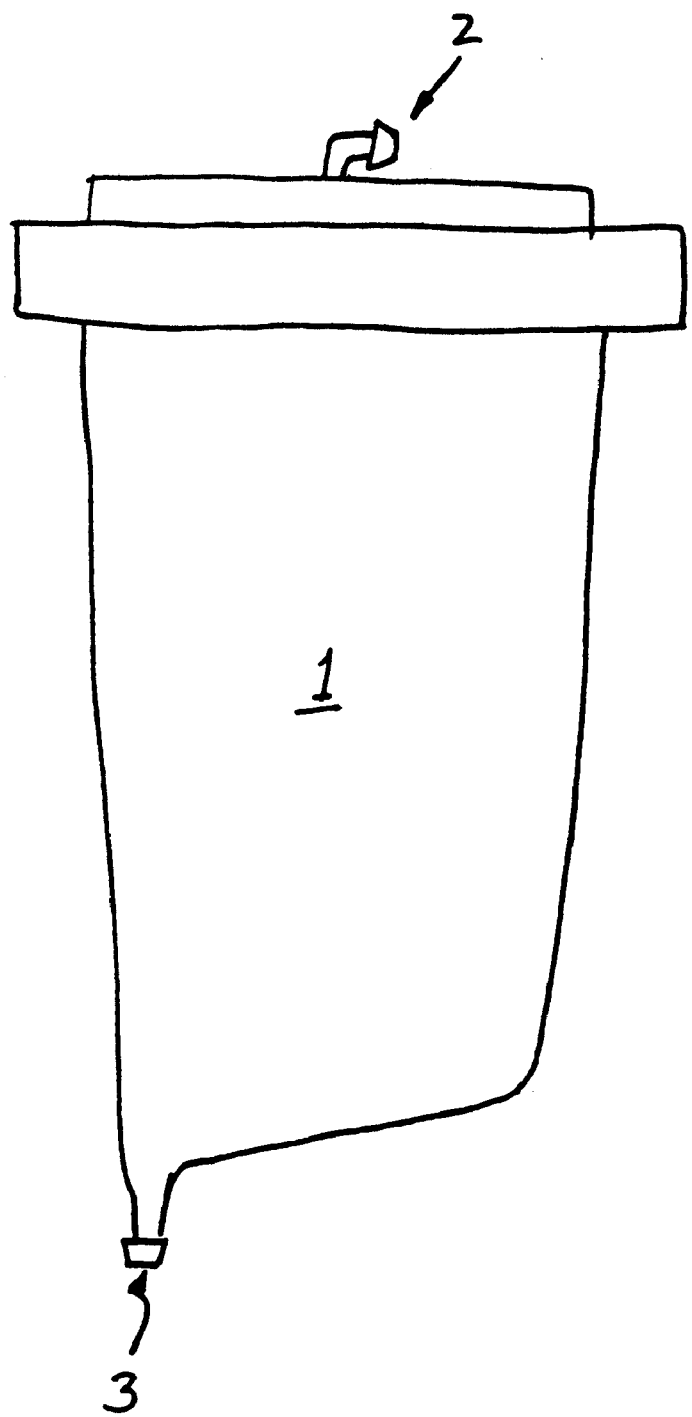
FIG. 1 is perspective view of an exemplary venous blood reservoir in accordance with the present invention.
Figure 2:
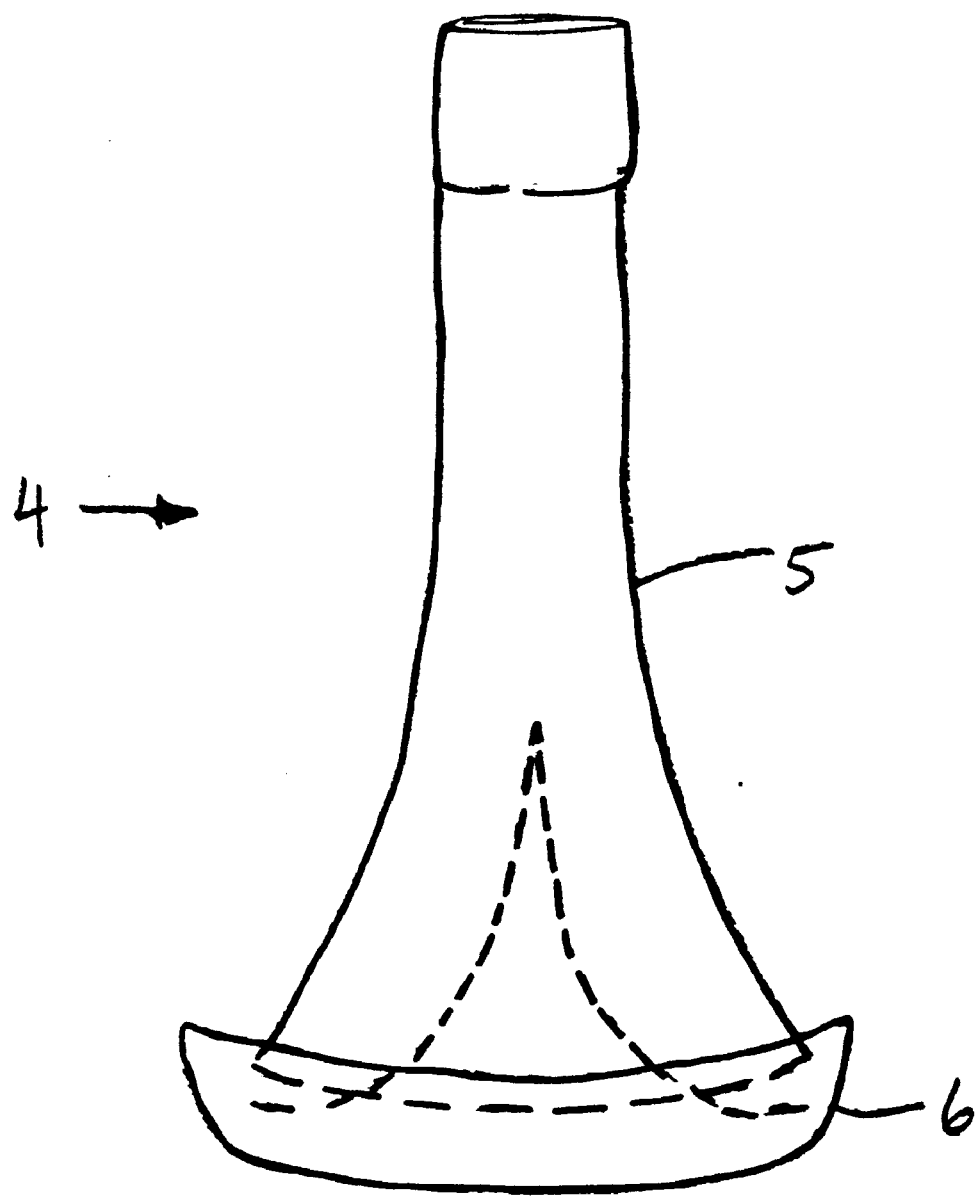
FIG. 2 is a cross-sectional view of a fluid control conduit of a blood reservoir in accordance with the present invention.

FIG. 2 illustrates one exemplary preferred embodiment of the fluid control conduit 4 of the present invention that may be used in conjunction with different types of reservoirs, including various combined cardiotomy and venous blood reservoirs or, for example, the venous blood reservoir shown in FIG. 1. In general, the fluid control conduit 4 comprises a nozzle 5 and a diverter or base 6. The preferred nozzle 5 is approximately in the shape of a cone, or trumpet, or other similarly shaped object having an internal radial diameter that increases in the downward/vertical direction along the length of the nozzle 5. The base 6 preferably has a center peak (shown by dotted lines in FIG. 2) and is shaped generally complimentary to the shape of the nozzle 5. The particular configuration of the nozzle 5, together with the preferred semi-cubicle parabolically-shaped base 6, decreases the venous blood velocity thereby reducing and/or preventing fluid turbulence and bubble formation. A more detailed description of the fluid control conduit of the present invention is given in the following exemplary embodiment of a combined cardiotomy fluid and venous blood reservoir.

FIGS. 3–6 demonstrate an exemplary embodiment of a cardiotomy fluid and venous blood reservoir 10 incorporating the fluid control conduit of the present invention. Reservoir 10 used to filter and defoam cardiotomy fluid and venous blood collected from a patient during a surgical procedure includes a housing 12 having a lower portion 14 with a side wall 16 and a lower wall 18 including a fluid outlet 20. The side wall 16 defines an upper edge portion 22 having an upper edge 24 at which a top part 26, including an optionally rotatable cap or turret assembly (generally indicated by reference numeral 28), may be sealingly received. Near its outer periphery, the cap) assembly 28 carries a plurality of circumferentially arrayed cardiotomy fluid inlets 32. The cardiotomy fluid inlets 32 are disposed radially or in parallel with a radius of the cap assembly 28. At its center, the cap assembly 28 carries a venous blood inlet 34, which is also rotatable as is indicated by arrowed numeral 36. Opposite to the cardiotomy inlets 32, the cap or turret assembly 28 also carries, for example, one or more venous blood inlets 34'.

Figure 3:
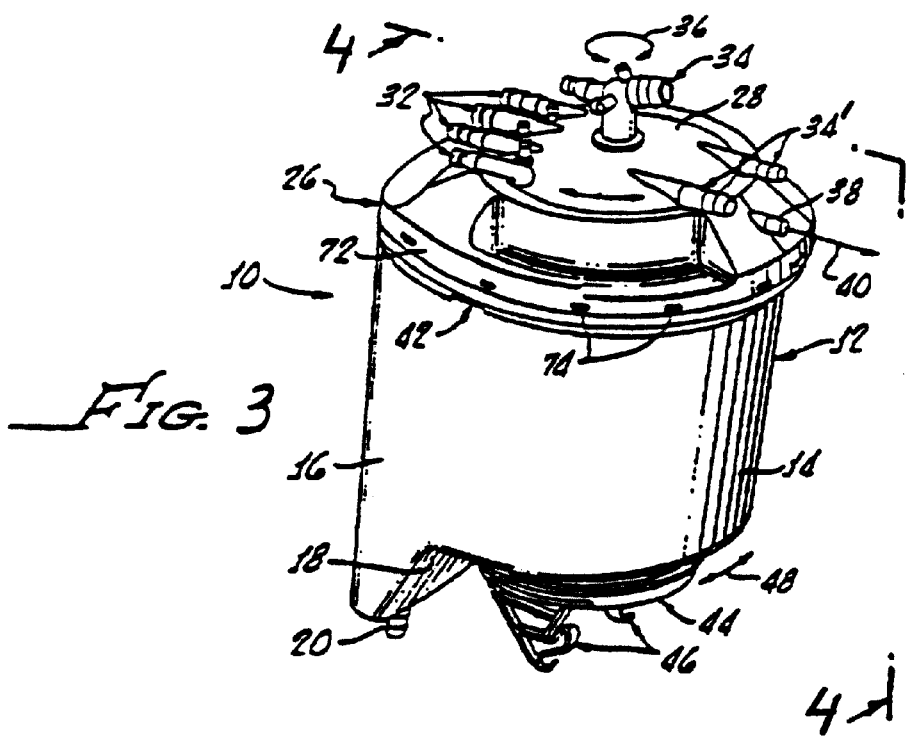
FIG. 3 is a perspective view of another preferred embodiment of an exemplary cardiotomy fluid and venous blood reservoir of the present invention.
Figure 4:
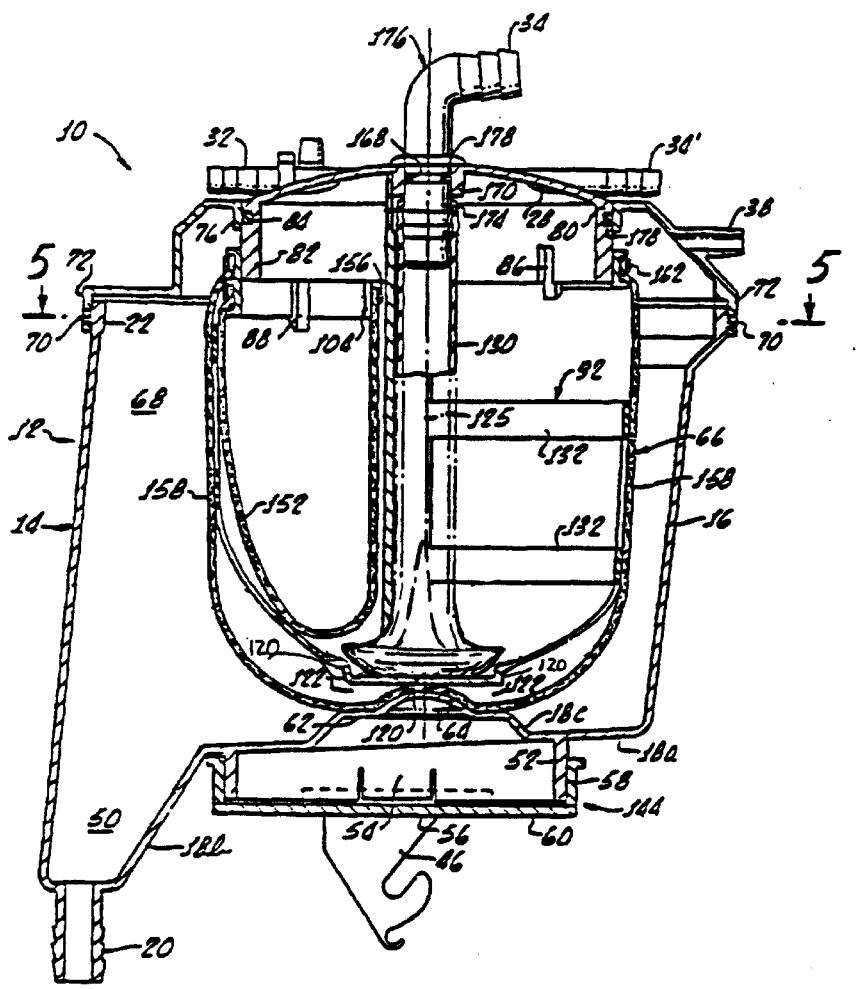
FIG. 4 is a cross-sectional side view taken along the line 4—4 of FIG. 3 of the exemplary cardiotomy fluid and venous blood reservoir of the present invention.

As shown in FIGS. 3, 4 and 6, the fluid inlets 34 are configured as right angle connectors. However, in a preferred embodiment, the fluid inlets 34 are arc-shaped and have an exemplary preferred radius of curvature in the range of 4–7.5 cm or any other sufficient radius to maintain a laminar fluid flow. The arc-shaped structure of the fluid inlets 34 helps to maintain a laminar flow of fluid from the tubing (not shown), through the inlets 32, 34 and into the reservoir 10, thereby reducing ol preventing bubble formation in the fluid. In addition, to further maintain a laminar fluid flow, it is preferred that the tubing and inlets 34 are assembled or manufactured in such a manner so that the junctions between the tubing, inlets and reservoir 10 have edge-free inner-surface connections. If, for example, the fluid flowing through the tubing encounters an edge of an inlet, the fluid laminar flow is disturbed by the juncture of the flexible venous return tubing and inlet 34 causing a random eddy-like flow. Therefore, in order to prevent turbulent fluid flow, the inlets 34 arc configured to have a sufficient radius of curvature to maintain a laminar to transitional fluid flow and the inner surfaces of the tubing, inlets 34 and reservoir 10 are edge-free.

Referring to FIGS. 3–6, the top part 26 of the housing 12 also includes a connector 38 which may be used as a vacuum connection or as an air vent. This connector 38 provides for fluid flow both inwardly and outwardly of the housing 12. As is indicated by arrowed numeral 40 on FIG. 3, when a vacuum is applied to the connector 38, air predominantly flows outwardly of the connector 38. The inlets 32, 34 and the connector 38 are of a hose-barb configuration to allow for convenient connection of the flexible hoses used during a surgical procedure for fluid flow of blood, body fluids and other fluids, as will be conventionally understood by those of ordinary skill in the art.

As shown in FIG. 3, the housing 12 defines a pair of opposite recesses 42 (only one of which is visible) so that the apparatus can be supported by a stirrup shaped bracket (not shown) extending from a support column (also not shown). The reservoir 10 may also include a lower hanging bracket 44 having a pair of depending hook-shaped portions 46, and which may be freely rotatable through, an angle of about 20 to 30 degrees, or more, as shown by arrowed numeral 48. The bracket 44 and hooks 46 allow attachment of an oxygenate/heat exchanger, if desired, to the reservoir 10 for convenient fluid flow interface therewith, while the relative rotational freedom (i.e. arrow 48) of this bracket allows the perfusionist to conveniently place and route fluid flow tubing and associated plumbing.

Figure 5:
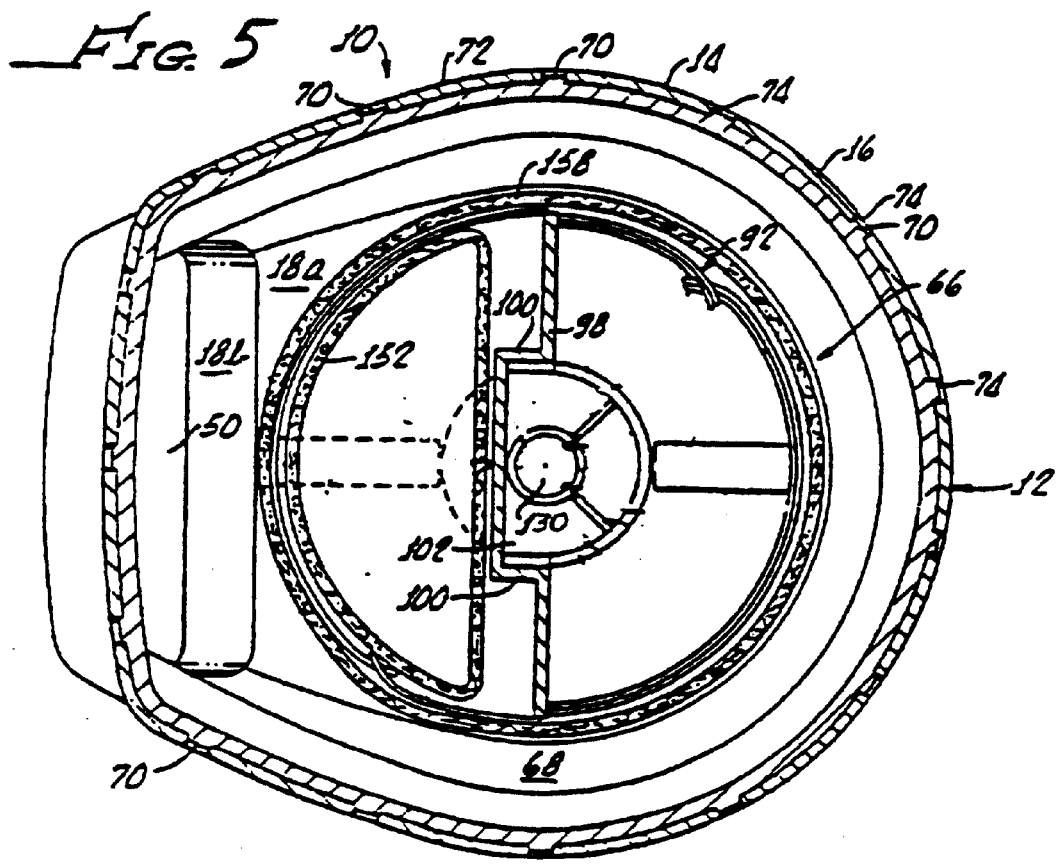
FIG. 5 is a cross-sectional plan view taken along the line 5—5 of FIG. 4 of the exemplary cardiotomy fluid and venous blood reservoir of the present invention.

With reference to FIGS. 3–5, the lower wall 18 of the lower housing portion 14 includes both a gently sloped wall part 18a and a more steeply sloped wall part 18b leading into a basin 50. The basin 50 communicates outwardly of the reservoir via outlet 20, which is also of a hose-barb configuration. From the wall portion 18a depends a circular lip 52 having a diametrically opposite pair of resilient pawl-fingers 54. Carried on this circular lip 52 by the fingers 54 is the bracket 44, which includes a circular central wall portion 56 carrying the hooks 46 and being carried by a circular upwardly extending peripheral wall portion 58. This peripheral wall portion 58 circumscribes the lip 52 and defines a pair of opposite outwardly opening slots 60 in which the fingers 54 are movably received to allow about 20 to 30 degrees of rotational freedom for the bracket 44.

Referring to FIG. 4, centrally of the portion 18a, the lower wall 18 defines an upwardly protruding portion 18c which leads to a plateau 62 where a crown or arcuate upward protrusion 64 of the wall portion 18 is disposed. A support, filter and defoamer assembly 66 is rotatably seated upon the crown 64. The support/filter assembly 66 is disposed within a chamber 68 cooperatively defined by the lower portion 14, top part 26, and cap part 28 of the reservoir 10.

The upper edge portion 22 of the lower portion 14 is rather thickened and defines a plurality of outwardly extending fingers 70. The top part 26 includes depending lip portion 72 which circumscribes the upper edge portion 22 of the lower portion 14, and which defines a plurality of outwardly opening apertures 74. The fingers 70 are received into the apertures 74 so that the top part 26 is retained on the lower portion 14. If desired, a sealing relation may be maintained between the top part 26 and lower portion 14 either by inclusion therebetween of a gasket material (not shown) or by use of a sealing material between these components. Thus, it will be appreciated that a vacuum communicated into the chamber 68 via a port 38 may be effective to maintain this chamber at a sub-ambient pressure, and to cause the collection of cardiotomy fluid and body fluids via the ports 32 and suction lines (not shown) attached thereto during or after a surgical procedure. Ordinarily, during a surgical procedure, the chamber 68 will be at a lower level than the patient, so that venous blood flows into the chamber by gravity and a vacuum is not necessary to draw this blood into the reservoir 10.

As is best seen in FIG. 6, the top part 26 includes a depending wall part 76 having a radially inwardly disposed surface 78 and defining an opening 80. The cap assembly or turret 28 is rotationally received in the opening 80, and includes a depending lip 82 which outwardly carries an o-ring, type of scaling member 84. The o-ring 84 engages a surface 78 to sealingly separate the chamber 68 from ambient while still allowing relative rotation of the turret 28. The lip 82 of the turret 28 includes two adjacent comparatively shorter pawl fingers 86 and two adjacent comparatively longer pawl fingers 88 which are each diametrically opposite to the shorter pawl fingers 86. As is best seen in FIGS. 4 and 6, the fingers 86, 88 engage an upper ring portion 90 of a support member 92 to thereby form a support filter and defoamer assembly 66.

The turret 28 also includes a pair of notches 94 which at their side edges engage respective buttresses 96 includes inwardly of the ring portion 90 at its junction with a transverse frame 98 extending diametrically from side to side within the ring portion 90 of the support member 92. Accordingly, the support filter and defoamer assembly 66 is rotationally coupled to the turret member 28 so that as the turret 28 is rotated to align the ports 32, the filter/defoamer assembly 66 also rotates within the housing 12 and chamber 68.

In an alternate embodiment of the device of the present invention, the turret 28 is stationary and is assembled onto the opening 80 via a snap fit. In another embodiment, the turret 28 is assembled onto the opening 80 using screws or other similar attachment components or devices. In yet another embodiment, the turret 28 and top part 26 are manufactured as a single component, thereby eliminating the subsequent steps of assembling the turret 28 onto the opening 80 of the top part 26.

Figure 7:
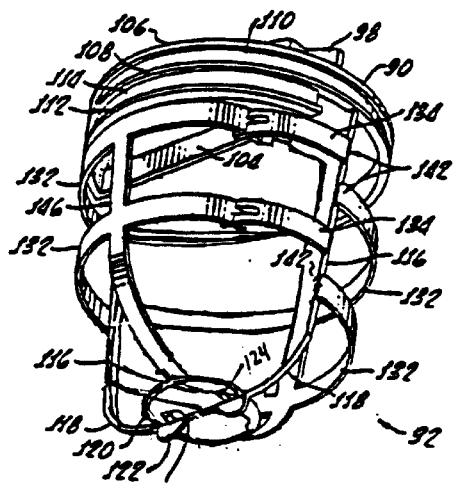
FIG. 7 is a perspective view of a component part of a blood reservoir in accordance with the present invention.

As shown in FIGS. 6 and 7, the support member 92 includes both the transverse frame portion 98, which is offset at parts 100 to define a vertically extending centrally located trough 102, and also includes a vertically extending short wall portion 104 extending from side to side and parallel to, but spaced slightly from, the frame portion 98. The depth of the trough 102 in the horizontal sense (i.c. the distance of the offset in frame 98) affects the areas of the final defoamer and element which will be exposed to cardiotomy fluid and venous blood flows, respectively. In the preferred embodiment illustrated, the offset of the frame portion 98 is such that one-half of the final defoamer element is exposed to each flow path. However, this need not be the case, and the offset can be selected to favor either flow path with a larger portion of the final defoamer element area according to the wishes of the designer.

The ring portion 90 of the support member 92 includes a pair of vertically spaced apart, radially outwardly extending ridges 106, 108 which cooperatively define a circumferentially continuous groove 110 circumscribing the ring portion 90. Below the ridge 108 is a second ridge 112 extending only about the vertically deeper portion of the ring portion 90 (i.e. terminating at wall 104), and cooperating, with the ridge 106 to define a groove 114 extending about halfway about the ring portion 90.

A bag 152 of depth filter material is secured at its open upper end 154 to the ring portion 90 and wall 104 by a tie strap 156 received about the bag 152 and into the groove 114. The tie strap 156 and a portion of the bag 152 adjacent to the open upper end 154 extend across the wall 104 between the terminations of the groove 114. The bag 152 functions as a first cardiotomy fluid defoamer element. In other words, the depth filter bag 152 is fabricated of a depth filter element material which has preferably been treated in order to render it effective as a first defoamer element acting on cardiotomy fluid and blood received into the bag 152. The bag 152 is configured to have sufficient height, depth and width so as to properly seat within a cavity of the support member 92.

Below the ring portion 90 of the reservoir 10, the frame portion 98 of the support member 92 includes opposing side edges 116 leading downwardly to an arcuate lower edge 118. Centrally of the lower edge 118 is disposed a horizontally extending ring-like portion 120 of the support member 92, which on its lower side carries two depending flange features 122. These flange features 122 straddle the crown 64 (indirectly, because other structure is interposed) to effectively locate the lower end of the support/filter and defoamer assembly 66 in the housing 12 while allowing relative rotation of this assembly 66. As shown in FIGS. 4 and 7, the flanges 122 include platforms 124 which define a type of support ledge for a central venous inflow conduit 130.

The above-described features of the combined cardiotomy and venous blood reservoir are strictly examplary and by no means limit the scope of the present invention as it relates to the fluid control conduit for use in a blood reservoir. One such fluid control conduit is described in detail with reference to FIG. 8.

Figure 8:
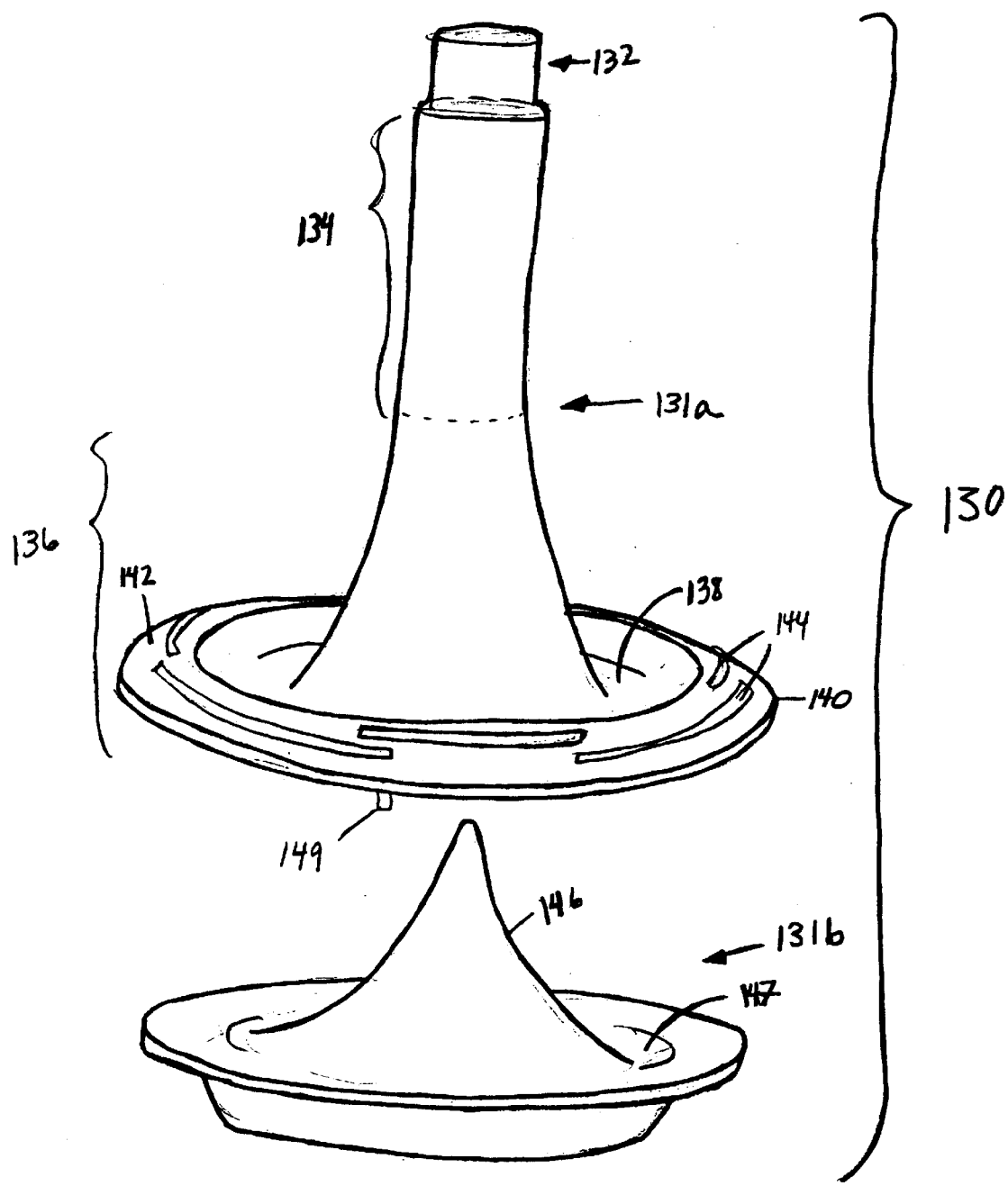
FIG. 8 is a perspective view of a fluid control conduit of the present invention.

Referring to FIG. 8, the fluid control conduit 130 comprises a nozzle 131a and a base 131b. In a preferred embodiment, the nozzle 131a and base 131b are made of polycarbonate, although other polymer materials such as high density polyethylene (HDPE), polyethylene terephthalate (PET) or polypropylene can also be used. The nozzle 131a has a minimum vertical height of approximately 12.1±1.0 cm. The upper end 132 of the nozzle 131a connects to the venous blood inlet 34 anti directs the downward flowing venous blood into and through the conduit 130. The general shape of the nozzle 131a resembles an inverted trumpet. The tubular shaped upper end 132 and middle portion 134 of the nozzle 131 may have an internal diameter in the range of approximately 1.63±0.05 cm. The internal diameter of the conduit 130 extends continuously and radially outward in the downward/vertical direction along its length. The fluid control conduit along the lower portion 136 of the nozzle 131 a reaches, for example, an internal diameter in the range of 5.5±0.5 cm at the underside of trough or channel 138 formed in the conduit 130. The gradual slope along the conduit 130 slows the fluid velocity and keeps the wall shear stress and turbulence very low and, as a result, prevents the formation of shear-induced platelet aggregates in the blood.

The outermost edge of the channel 138 extends continuously and radially outward in a relatively horizontal direction to thereby form a lip 140 along the lower portion 136 of the conduit 130. The channel 138 and lip 140 of the nozzle 131a serve the function of dividing and separating the entrained venous return blood from that of the filtered cardiotomy fluid in the reservoir 10. The upper surface 142 of the lip 140 includes a series of raised concentric ring-portions 144. The purpose of these ring-portions 144 is to provide for fluid venting at the bottom of the depth filter bag 152 that is mounted above and in intimate contact with the ring-portions 144 of the nozzle 131a. The raised concentric ring-portions 144 are offset from one another to prevent cardiotomy fluid retention between the ring-portions 14 and bag 152. In addition, each ring-portion 144 is chamfered which permits the lower portion 136 of the conduit 130 to rotate with the venous blood inlet 34 without tearing or damaging the filter bag 152 or snagging the filter bag 152 on the support member 92.

Alternatively, as previously described in relation to FIG. 2, the conduit 130 of the present invention can also be used in a reservoir in which only one fluid type is collected, as, for example, a venous blood reservoir. When used in a single fluid reservoir, the nozzle 131a of the conduit 130 does not require the fluid separating feature of the lip portion 140. As a result, the shape of the nozzle 131a for a single-fluid reservoir is approximately cone-shaped, as opposed to a multiple fluid reservoir that is approximately trumpet-shaped. However, whether cone-shaped or trumpet-shaped, the internal radial diameter of the nozzle increases in the downward/vertical direction along the length of the nozzle 5.

Still referring to FIG. 8, the base 131b of the fluid control conduit 130 comprises an axially aligned center peak 146 shaped generally as an inverted cone or, more particularly, a semicubicle parabola with its vertex forming the center peak. The sides or walls of the center peak 146 slope gently first in a downward and radially outward direction and then in a slight upward and radially outward direction, thereby forming a trough 147 in the lower portion of the base 131b. When assembled together, the tip of the center peak 146 of the base 131b extends axially within the lower portion 136 of the conduit 130. One or more standoffs 149 located on the underside of the lip 140 of the lower portion 136 of the nozzle 131a define both a horizontally extending separating edge and a vertically extending locating edge, having a height in the range of approximately 1–3 mm, for the base 131b of the conduit 130. The standoffs 149 function to properly locate and/or guide the base 131b onto the nozzle 131 a of the conduit 130. When properly located, the trough 147 of the base 131b is aligned with the trough 138 of the nozzle 131a. Consequently, a trap feature is formed which prevents the reflux of air or other gases upwardly into the nozzle 131a of the conduit 130. During normal use of the reservoir 10, the conduit 130 runs full of venous blood and, as a result, both turbulence of the blood as well as the possibility of an air embolism from air reflux into the circulatory system are prevented.

The center peak 146 of the conduit 130 also functions to divert the downward flowing venous blood in the nozzle 131a into the base 131b at an optimum fluid velocity to overcome the buoyancy effect of air or, as bubbles within the blood. This, in turn, prevents the formation or generation of smaller bubbles which are typically generated from the considerable fluid turbulence and free surface created from larger air or gas bubbles. Further, the exit path of the blood in the base 131b never encounters an upward fluid exit path angle that is greater than approximately 45 degrees from horizontal, thereby preventing the rise of bubbles through a liquid chamber. As a result, the fluid flow path is relatively free of discharge turbulence and dynamic liquid retention, thereby resulting in little or no bubble formation.

Referring to FIGS. 6 and 7, a two-part defoamer bag structure 158 is placed about the support structure 92. At its open upper end 160, the bag structure 158 is secured to a ring portion 90 by a tie strap 162 received into a groove 110. The bag structure 158 at its closed lower extent is received slidably (i.e. rotationally) on the crown 64 and is conformable to this crown to allow the flanges 122 to effect rotational positioning of the support/filter and defoaming structure 66 at its lower end. The defoamer bag structure 158 is formed of an inner bag 164 of open-cell reticulated polyurethane material, and an outer bag 166 of mesh fabric material. As is known in the art, the polyurethane material is treated with a silicone or other effective defoaming agent.

Referring to FIGS. 4 and 6, it is seen that the turret 28 defines a central opening 168 circumscribed by a downwardly extending wall 170. Rotationally received in the opening 168 is a stem portion 174 of a fitting 176. This fitting 176 defines the venous blood inlet 34, and carries an o-ring type of sealing member 178. The o-ring sealing member 178 engages the surface of the wall portion 170 to allow relative rotation of the fitting 176 independently of rotation of turret member 28, and independently of the housing 12.

Having observed the structure of the combined cardiotomy fluid and venous blood reservoir 10 as described above, its operation and use in a surgical procedure will be apparent to those ordinarily skilled in the art. As schematically shown in FIG. 9, it is seen that a branched flow path 182 extends from inlets 32, 34 to outlet 20. At the inlet 32, the notation "C.F.IN" means that cardiotomy fluid is received in this inlet. Similarly, at inlet 34, the notation "V.IN" means that venous blood is received in this inlet. The flow path 182 is confluent so that the path from inlet 32 and the path from inlet 34 are tributaries to the flow from outlet 20. In a preferred embodiment of the invention, the flow received in inlet 32 is first exposed to depth filter material 152 which appears to include a filter element 152', but which also includes an effective defoaming action 152". Consequently, the cardiotomy fluid is effectively defoamed and filtered simultanously,. Fluid in the cardiotomy branch next flows to and through a respective portion of the defoamer element 158 and is subjected to another defoaming step. Similarly, on the venous blood side of flow path 182, the blood is defoamed by a respective part of defoamer element 158. Next, the flow paths form a juncture 182' and the defoamed fluid from both branches flows from outlet 20.

The present invention also provides a method of treating venous blood in a blood reservoir that decreases fluid turbulence and bubble formation. In an exemplary embodiment of such a method, venous blood is first channeled into a reservoir through one or more inlets. Next, the venous blood then flows through a nozzle of a fluid control conduit of the reservoir. In a preferred embodiment, the nozzle has an internal radial diameter that increases in the downward/vertical direction along the length of the nozzle. In addition, the venous blood flows through the nozzle at an optimum fluid velocity to, thereby, overcome the buoyancy effect of air or gas bubbles within the blood. The venous blood is then directed between a lower portion of the nozzle and a base of the fluid control conduit.

The method of treating venous blood may further include the steps of defoaming the blood by flowing the blood through a defoamer element and venting the venous blood as it passes through the lower portion of the nozzle and the base of the conduit. In addition, a trap may be used to prevent reflux of air or gas into the nozzle of the conduit.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A blood conduit of a blood reservoir, said blood conduit comprising:
   a base including an axially aligned center peak and a trough formed in the lower portion of said base; and
   a nozzle having an internal radial diameter that increases in a downward/vertical direction along a length of said nozzle, wherein an upper end of said nozzle connects to a blood inlet and a lower portion of said nozzle is aligned with and located onto said base.

2. The blood conduit of claim 1 wherein said nozzle is shaped to resemble an inverted cone.

3. The blood conduit of claim 1 wherein said nozzle is shaped to resemble an inverted trumpet.

4. The blood conduit of claim 1 wherein said base is shaped as a semicubicle parabola.

5. The blood conduit of claim 1 wherein a gradual slope along said conduit keeps a low wall shear stress of said conduit.

6. The blood conduit of claim 1 wherein a gradual slope along said conduit reduces fluid velocity of said conduit.

7. The blood conduit of claim 3 wherein a lower portion of said nozzle includes a channel and an outermost edge of said channel extends continuously and radially outward in a relatively horizontal direction.

8. The blood conduit of claim 7 wherein said outermost edge of said channel forms a lip along said lower portion of said nozzle.

9. The blood conduit of claim 8 wherein said reservoir is a combined cardiotomy fluid and venous blood reservoir and said channel and said lip separate said venous blood from said cardiotomy fluid in said reservoir.

10. The blood conduit of claim 8 wherein said lip includes a series of raised concentric ring-portions.

11. The blood conduit of claim 10 wherein said ring portions are offset from one another along said lip.

12. The blood conduit of claim 10 wherein said ring portions are chamfered to prevent snagging.

13. The blood conduit of claim 1 wherein said fluid control nozzle is made of a polymer material.

14. The blood conduit of claim 1 wherein said fluid control nozzle is made of polycarbonate.

15. The blood conduit of claim 1 wherein said reservoir is a combined cardiotomy fluid and venous blood reservoir.

16. The blood conduit of claim 1 wherein said reservoir is a venous blood reservoir.

17. The blood conduit of claim 1 wherein said nozzle includes one or more standoffs to locate and guide said base onto said nozzle.

18. A method of treating venous blood in a blood reservoir, said method comprising:
    channeling said venous blood into a reservoir through one or more inlets at an upper end thereof;
    flowing said venous blood through a nozzle having an internal radial diameter that increases in a downward/vertical direction along a length of said nozzle of a conduit; and
    directing said venous blood between a lower portion of said nozzle and a base of said conduit, whereby the base includes an axially aligned center peak and a trough formed in the lower portion of said base.

19. The method of claim 18 further including defoaming said venous blood by flowing said venous blood through at least one defoamer element.

20. The method of claim 18 further including flowing said venous blood out of an outlet of said reservoir.

21. The method of claim 18 wherein said base is shaped as a semicubicle.

22. The method of claim 18 further including venting said venous blood as said venous blood passes through said lower portion of said nozzle and said base of said conduit.

23. The method of claim 18 further including preventing reflux of air or gas upwardly into said nozzle via a trap.

24. The method of claim 18 wherein said flowing of said venous blood through said nozzle is accomplished at an optimum fluid velocity to overcome the buoyancy effect of air or gas bubbles within said venous blood.

25. The method of claim 18 wherein said nozzle is shaped to resemble an inverted cone.

26. The method of claim 18 wherein said nozzle is shaped to resemble an inverted trumpet.

* * * * *